United States Patent [19]

Reese

[11] Patent Number: 5,436,331
[45] Date of Patent: Jul. 25, 1995

[54] PROTECTION OF HYDROXY FUNCTION WITH 1-N-ARYL-4-ALKOXY-PIPERIDIN-4-YL

[75] Inventor: Colin B. Reese, London, United Kingdom

[73] Assignee: Kings College London, London, United Kingdom

[21] Appl. No.: 38,213

[22] Filed: Mar. 29, 1993

Related U.S. Application Data

[62] Division of Ser. No. 246,540, Sep. 14, 1988.

[30] Foreign Application Priority Data

Mar. 24, 1986 [GB] United Kingdom ............... 8607265

[51] Int. Cl.$^6$ ............... C07H 19/067; C07H 19/167
[52] U.S. Cl. .................................. 536/55.3; 536/25.3
[58] Field of Search .................... 536/25.3, 55.3, 25.3

[56] References Cited

U.S. PATENT DOCUMENTS 4,157,573 9/1979 Himmele et al. .............. 424/267

OTHER PUBLICATIONS

Taylor et al. Synthesis, pp. 606–608, 1981.
Gallagher et al. J. Chem. Soc. pp. 5110–5120, 1962.
Reese et al. Tetrahedron Letters 27:2291–2244, 1986.
Narang et al. Total Synth. Nat. Prod. 6:51–84, 1984.
Casy, Chem. Abstr. No. 61:8267c, Sep., 1964, Experientia, 20(8):437–438, 1964.
Brookes et al, Chem. Abstr. No. 51:17909a, Nov., 1957, J. Chem. Soc., pp. 3173–3175, 1957.
Reese et al. Tetrahedron Lett. 25, 3015, 1984.

*Primary Examiner*—Douglas W. Robinson
*Assistant Examiner*—Gary L. Kunz
*Attorney, Agent, or Firm*—Shoemaker and Mattare, Ltd.

[57] ABSTRACT

A process for protecting the 2′-hydroxyl of a nucleoside, which can then be used in the chemical synthesis of polyribonucleotides, comprising the reacting of a protected nucleoside of formula I

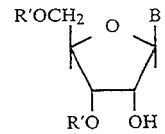

wherein B is a nucleoside heterocyclic base and R′ is a hydroxyl-protecting group, with 1-N-aryl-4-alkoxy-1,2,5,6-tetrahydropiperidine of formula II

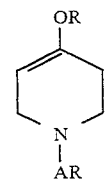

wherein Ar is an aryl group possessing an electron-withdrawing substituent which renders said protecting group acid labile and R is $C_1$–$C_4$ alkyl, in the presence of an acid catalyst and a solvent to yield the compound of formula II below:

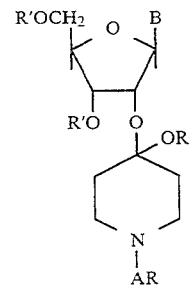

1 Claim, No Drawings

PROTECTION OF HYDROXY FUNCTION WITH 1-N-ARYL-4-ALKOXY-PIPERIDIN-4-YL

This is a division of application Ser. No. 07/246,540, filed Sep. 14, 1988.

This invention relates to protecting groups for organic synthesis; more particularly it relates to acetal groups suitable for the protection of 2'-hydroxy functions in rapid oligoribonucleotide synthesis.

A 4-methoxytetrahydropyran-4-yl group has proved to be particularly suitable for the protection of 2'-hydroxy functions in oligoribonucleotide synthesis in solution. In the development of methods for the rapid synthesis of oligo- and poly-ribonucleotides both on solid supports and in solution, for reasons of practical convenience, it is advisable to use a modified trityl group, such as 4,4'-dimethoxytrityl or 9-phenylxanthen-9-yl, to protect terminal 5'-hydroxy functions. It has recently been shown that the relatively drastic protic acid conditions required for the removal of a 5'-O-(9-phenylxanthen-9-yl) group from a fully-protected dinucleoside phosphate lead to appreciable concomitant removal of the 2'-O-(4-methoxytetrahydropyran-4-yl) group. In order to overcome such problems, there is a need for a better protecting group, more particularly for an alternative to 4-methoxytetrahydropyran-4-yl.

A 1-methoxycyclohex-1-yl group has been found to be much too acid-labile to be of use in oligoribonucleotide synthesis. However, acetals may be stabilized to acidic hydrolysis by the introduction of electron-withdrawing groups. For example, 2'-O-(4-methoxytetrahydropyran-4-yl)-uridine undergoes acid-catalyzed hydrolysis at a rate that is more than two orders of magnitude slower than that of the corresponding 1-methoxycyclohex-1-yl-protected compound. Later studies on the hydrolysis of 5'-protected thymidine derivatives suggested that the replacement of O by S in the six-membered ring of 2'-O-(4-methoxytetrahydropyran-4-yl)-uridine would increase the rate of acetal hydrolysis by a factor of ca 5, whereas the replacement of the same oxygen atom by a sulphone group would decrease the rate of hydrolysis by a factor of more than 400.

Given that it is desirable to retain an acid-labile group for the protection of 2'-hydroxy functions, an object of the present invention was to design weakly basic 1-N-substituted-, preferably 1-N-aryl-, 4-alkoxy-, preferably 4-methoxy-, piperidin-4-yl groups, which, for example, at pH 2-2.5, would be unprotonated to a significant extent on N-1 and thus as labile as, say, the 4-methoxytetrahydropyran-4-yl group, but which, under the more strongly acidic conditions required for the removal of, say, the 9-phenylxanthen-9-yl protecting group, would be largely protonated and perhaps therefore have a similar stability to acidic hydrolysis as the sulphone system referred to above. Certain groups have now surprisingly been found which exhibit essentially the desired advantageous properties.

The present invention provides a method of organic synthesis comprising the protection of a hydroxy function characterised in that a 1-N-substituted-4-alkoxypiperidin-4-yl group is used as the protecting group.

More particularly the present invention relates to such a method wherein a 1-N-aryl-4-alkoxy-piperidin-4-yl group is used to protect a 2'-hydroxy function in an oligo- or poly-ribonucleotide synthesis.

In a preferred embodiment, the present invention relates to the use as a protecting group for organic synthesis, in particular for 2'-hydroxy functions in oligo-ribonucleotide synthesis, of groups corresponding to the following general formula:

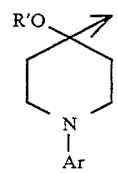

wherein

R' independently represents alkyl, preferably $C_1$–$C_4$ alkyl, typically methyl; and Ar independently represents monocyclic aryl, preferably phenyl, having an, preferably one, electron-withdrawing substituent, for example, halogeno, typically fluoro or chloro, and optionally one or more further substituents, for example $C_1$–$C_4$ alkyl, typically methyl.

As preferred examples of such groups, there may be mentioned the 1-N[(2-chloro-4-methyl)phenyl]-4-methoxy-piperidin-4-yl and 1-N(2-fluorophenyl)-4-methoxy-piperidin-4-yl groups:

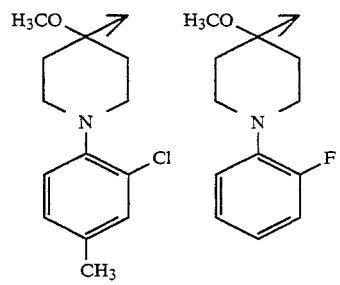

As will be appreciated by those skilled in the art, other effective, possibly more effective, groups may result, for example, by exchanging Cl for F or Br, and/or $CH_3$ for $C_2H_5$ or H.

The present invention also provides compounds comprising hydroxy functions which have been protected by the present groups. Moreover, it relates to the production thereof.

The present invention is, for example, applicable to hydroxy group-containing carbohydrates or derivatives thereof, such as sugars, in particular ribonucleosides and RNA. It is especially useful in the preparation of monomers and dimers, for example, which are to be used in producing oligo- and poly-ribonucleotides by chemical synthesis.

In accordance with the present invention, groups corresponding to the first general formula may be derived from the corresponding enol ethers:

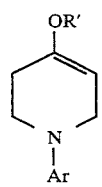

wherein

R' and Ar are as defined above;

under reaction conditions suitable for producing the correspondingly-protected hydroxy compounds, such as correspondingly-2'-protected ribonucleosides.

The enol ethers may be obtained by known processes, for example by alcohol extrusion, such as by heating with toluene-4-sulphonic acid (TsOH), of corresponding dialkyl acetals:

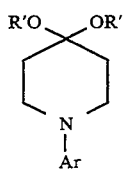

wherein

R' and Ar are as defined above.

Such dialkyl acetals may be obtained, inter alia, from the corresponding piperidin-4-ones:

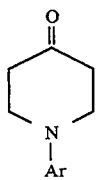

wherein

Ar is as defined above;
by reaction with, for example, (R'O)₃CH, wherein R' is as defined above, in the presence of toluene-4-sulphonic acid and an alcohol solvent (R'OH), such as methanol, under reflux.

In use, the present protecting groups result in compounds corresponding to the following general formula:

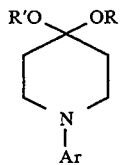

wherein

Ar and R' are as defined above; and

R represents the residue of the protected hydroxy compound, for example a 2'-deoxy residue of a natural ribonucleoside.

Such protected compounds may be obtained by reacting the organic hydroxy compound, which is to be protected, with the above-defined enol ether, for example, in the presence of an acid catalyst, such as CF₃COOH, in a solvent, such as dioxane.

In accordance with the present invention, the protected compounds may be further reacted by conventional means to form oligo- and poly-nucleotides, for example.

The following illustrates the present invention:

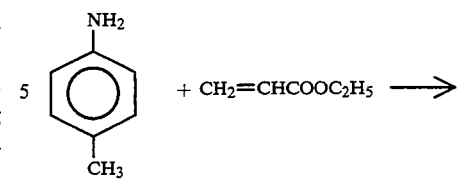

A mixture of p-toluidine (300 g), ethyl acrylate (833 g), glacial acetic acid (320 ml) and cuprous chloride (56.1 g) was refluxed under nitrogen for 20 hours.

A solution of the cold mixture in ether (700 ml) was shaken with water (2×500 ml) and with water-aqueous ammonia (d 0.88), (1:1 v/v; 3×250 ml). The solvent was removed from the MgSO₄-dried ethereal layers and unreacted starting material was removed by distillation using a water pump.

The residue was fractionated by distillation to give a fraction (90 g) with b.p. 125°–158° C./0.4 mm Hg (0.52 mbar) and pure N,N-di-(2-ethoxycarbonylethyl)-p-toluidine (644 g) with b.p. 162°–164° C./0.4 mm Hg (0.52 mbar).

This was then converted to ethyl 1-N-(p-tolyl)-piperidin-4-one-3-carboxylate:

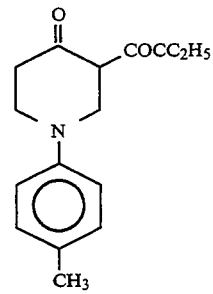

A 3 liter three-necked flask was equipped with a dropping funnel, a mercury-seal stirrer and a water-cooled condenser with a gas-trap connected on the top. It was charged with sodium hydride (obtained by washing 30 g of 80% sodium hydride dispersion in mineral oil with dry benzene). Dry benzene (800 ml) was added, stirring was started and N,N-di-(2-ethoxycarbonylethyl)-p-toluidine (153.5 g) was added slowly. On addition of absolute alcohol (1.6 ml), evolution of hydrogen started immediately. The condensation generated sufficient heat to cause the benzene to reflux.

After one hour, glacial acetic acid (57.26 ml) was added, followed by water (48 ml). After the reaction mixture had been allowed to stand for ca 15 minutes, it was filtered and the residue washed with benzene (2×50 ml). The combined filtrate and washings were placed in a flask and the solvent was removed; the crude product was dissolved in chloroform, washed with water and dried over MgSO₄. The solvent was removed to give 122.1 g of crude product (mp 71°–72° C.).

This was then converted to 1-N-(p-tolyl) piperidin-4-one:

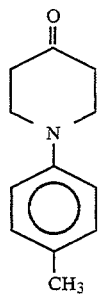

A solution of the keto-ester (21.0 g) in concentrated hydrochloric acid-water (5:4 v/v; 100 ml) was refluxed for 2 hours, concentrated under reduced pressure to ca. 50 ml and basified with 60% aqueous sodium hydroxide and extracted with ether (2×100 ml).

The concentrated extracts were dried over MgSO₄ and the solvent removed; the crude ketone was distilled to give 11.66 g of product (bp 120°–121° C./0.05 mm Hg (0.065 mbar)).

(The above 1-N-(p-tolyl)-piperidin-4-one may also be prepared by an improved procedure that is suitable for the synthesis of a variety of 1-N-aryl-piperidin-4-ones in accordance with the present invention, including examples in which the aryl group is halogenated. This alternative production will be illustrated below.)

The 1-N-(p-tolyl)-piperidin-4-one was then converted to 1-N-[(2-chloro-4-methyl)phenyl]-piperidin-4-one:

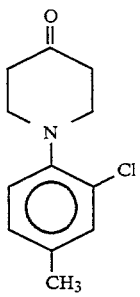

A solution of 1-N-(p-tolyl)-piperidin-4-one (70 g), and N-chlorosuccinimide (61.6 g) in dry dichloromethane (300 ml) was gently refluxed. After ca 3 hours, when about 90% of the starting material had reacted, the solution was cooled and washed with a saturated solution of sodium hydrogen carbonate (3×100 ml). The organic layer was separated and then washed with a solution of 5M hydrochloric acid (3×80 ml).

The combined acidic extracts were cooled in an ice-water bath and carefully neutralized with 1M aqueous sodium hydroxide.

The products were extracted with chloroform (3×200 ml) and the combined extracts were dried over MgSO₄. The solvent was then removed under reduced pressure to give an orange-red viscous oil.

By distillation of this material, 57.4 g of a fraction (bp 118°–120° C./0.05 mm Hg (0.065 mbar)) was obtained. This product solidified and was recrystallized from petroleum ether (bp 40°–60° C.) to give colourless needles (mp 65°–66° C.).

The 1-N-[(2-chloro-4-methyl)phenyl]-piperidin-4-one was then converted to 1-N-[(2-chloro-4-methyl)phenyl]-4,4-dimethoxypiperidine:

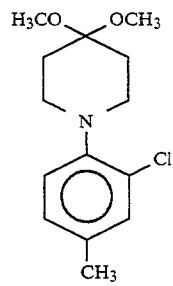

A dry 200 ml round-bottomed flask, fitted with a water-cooled condenser and a calcium chloride tube, was charged with 1-N-[(2-chloro-4-methyl)phenyl]-piperidin-4-one (5.0 g), trimethyl orthoformate (2.94 ml), toluene-4-sulphonic acid (4.68 g) and AR methanol (50 ml). The reaction was heated under reflux. After 10 minutes, the products were cooled (ice-water bath), neutralised with a 30% solution of sodium methoxide in methanol and the products were concentrated under reduced pressure. Dichloromethane (75 ml) was added to the residue and the resulting mixture was washed with saturated aqueous sodium hydrogen carbonate. The dried (MgSO₄) organic layer was evaporated under reduced pressure to give the required product (5.75 g), which had mp 58° C. after crystallisation from petroleum ether (bp 40°–60° C.).

The 1-N-[(2-chloro-4-methyl)phenyl]-4,4-dimethoxypiperidine was then converted to the following enol ether:

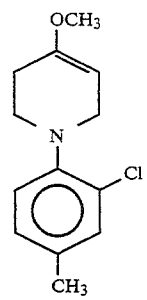

1-N-[(2-chloro-4-methyl)phenyl]-4,4-dimethoxypiperidine (10.0 g) and toluene-4-sulphonic acid (0.071 g) were dissolved in dry dichloromethane and then the solvent was removed under reduced pressure. The flask was provided with a magnetic stirrer and connected to a water pump, placed in an oil bath (150° C.) and heated under reduced pressure (20 mm Hg (26 mbar)) for 45 minutes.

The products were then cooled (ice-water bath), diluted with dry dichloromethane (25 ml) and neutralised with NaOCH₃/CH₃OH. The resulting solution was washed with a saturated solution of NaHCO₃ and then dried (MgSO₄). Evaporation of the solvent gave the crude product (6.23 g) which was then distilled and had bp 140° C./0.005 mm Hg (0.0065 mbar).

The above-mentioned improved synthesis of 1-N-aryl-piperidin-4-ones involves a two-step procedure starting from an aromatic primary amine (ArNH₂) and 1,5-dichloropentan-3-ol. When the latter are heated together in the presence of potassium carbonate in dimethylformamide, 1-N-aryl-piperidin-4-ols are obtained in good yields. These compounds are then oxidized to the corresponding 1-N-aryl-piperidin-4-ones. This improved route may be summarized as follows:

TABLE 1

| | Synthesis of 1-N-aryl-piperidin-4-ols | | | |
|---|---|---|---|---|
| Substrate | Reaction Time (hr) | Yield (%) | m.p. (°C.) | b.p. (°C./mm Hg) |
| 2-FC₆H₄NH₂ | 1.0 | 70 | — | 102–108/0.02 |
| 4-MeC₆H₄NH₂ | 1.5 | 83 | 83 | — |
| 4-ClC₆H₄NH₂ | 1.0 | 77 | 99–101 | — |
| 3-ClC₆H₄NH₂ | 1.5 | 54 | — | 148–152/0.07 |
| 2-ClC₆H₄NH₂ | 1.5 | 32 | — | 136–142/0.2 |
| 3-Cl,4-MeC₆H₃NH₂ | 2.0 | 65 | 56–57 | — |

Experimentally, in order to obtain 1-N-aryl-piperidin-4-ols, 1,5,-dichloropentan-3-ol, see Kelson, R., and Robson, R., Coord. Chem., 1979, 6, 235, (1.0 mol. equiv), primary aromatic amine (1.1 mol. equiv.), anhydrous potassium carbonate (2.2 mol. equiv.), sodium iodide (0.55 mol. equiv.) and anhydrous dimethylformamide (DMF, 3.5 ml/gram of aromatic amine) are heated together at 100° C., under nitrogen, with vigorous stirring. The cooled products are partitioned beteen ether (3.5 ml/gram of aromatic amine) and the same volume of water. After separation, the aqueous layer is extracted twice with an equal volume of ether. The combined organic layers are then extracted five times with equal volumes of saturated brine. The organic layer is dried (MgSO₄) and evaporated under reduced pressure. The residue obtained is purified either by distillation or by recrystallization.

TABLE 1

| | Synthesis of 1-N-aryl-piperidin-4-ols | | | |
|---|---|---|---|---|
| Substrate | Reaction Time (hr) | Yield (%) | m.p. (°C.) | b.p. (°C./mm Hg) |
| 2-FC₆H₄NH₂ | 1.0 | 70 | — | 102–108/0.02 |
| 4-MeC₆H₄NH₂ | 1.5 | 83 | 83 | — |
| 4-ClC₆H₄NH₂ | 1.0 | 77 | 99–101 | — |
| 3-ClC₆H₄NH₂ | 1.5 | 54 | — | 148–152/0.07 |
| 2-ClC₆H₄NH₂ | 1.5 | 32 | — | 136–142/0.2 |
| 3-Cl,4-MeC₆H₃NH₂ | 2.0 | 65 | 56–57 | — |

In order to obtain 1-N-aryl-piperidin-4-ones, see Taylor, E. C., and Skotnicki, J. S., Synthesis, 1981, 606, trifluoroacetic acid (TFA, 0.5 mol. equiv.) is added dropwise to a vigorously stirred solution of 1-N-aryl-piperidin-4-ol (1.0 mol. equiv.), N,N'-dicyclohexylcarbodi-imide (DCC, 2.0 mol. equiv.), pyridine (1.0 mol. equiv.) in dimethyl sulphoxide (DMSO, 600 ml/mol. of 1-N-aryl-piperidin-4-ol) and benzene (1600 ml/mol. of 1-N-aryl-piperidin-4-ol) under nitrogen at 0° C. (ice-water bath). The reaction is then allowed to proceed, with continuous stirring, at room temperature. After 24 hr., the products are filtered and the residue is washed with a small volume of ether. The combined filtrate and washings are then extracted with 4M hydrochloric acid (3 liters/mol. of 1-N-aryl-piperidin-4-ol). The aqueous layer is basified (to ca. pH 8) by the careful addition of 4M aqueous sodium hydroxide and the resulting mixture is extracted with ether (3 liters/mol. of 1-N-aryl-piperidin-4-ol). The combined organic extracts are washed with saturated brine (5×1 liters mol. of 1-N-aryl-piperidin-4-ol) dried (MgSO₄), and evaporated under reduced pressure. The residue obtained is purified either by distillation or recrystallization.

TABLE 2

| Synthesis of 1-N-aryl-piperidin-4-ones | | | |
|---|---|---|---|
| Aromatic substituents | Yield (%) | m.p. (°C.) | b.p. (°C.) |
| 2-F | 67 | 64 | — |
| 4-Cl | 83 | 55–56 | ~160/0.3 mm Hg |
| 3-Cl | 60 | — | 120–130/0.004 mm Hg |
| 2-Cl | 76 | 80 | 105–110/0.13 mm Hg |
| 3-Cl, 4-Me | 74 | — | 160/0.1 mm Hg |
| 4-Me | 72 | — | 106/0.1 mm Hg |

The general procedure for the conversion of 1-N-aryl-piperidin-4-ones to the required enol ethers (ie. 1-N-aryl-4-methoxy-1,2,5,6-tetrahydropyridines) also inolves two steps. In the first step, the ketones are converted to their dimethyl acetals (the corresponding conversion of 1-N-[(2-chloro-4-methyl)phenyl]-piperidin-4-one to 1-N-[(2-chloro-4-methyl)phenyl]-4,4-dimethoxypiperidine is exemplified above and see also the general experimental procedure below for acetal preparation, together with Table 3). In the second step, methanol is extruded to give the required enol ethers (the corresponding conversion of 1-N-[(2-chloro-4-methyl)-phenyl]-4,4-dimethoxypiperidine to 1-N-[(2-chloro-4-methyl)phenyl]-4-methoxy-1,2,5,6-tetrahydropyridine is exemplified above and see also the general experimental procedure below for enol ether preparation, together with Table 4). This route may be summarized as follows:

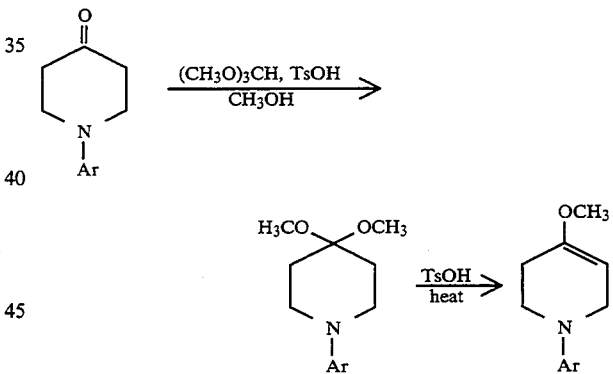

Experimentally, in order to obtain 1-N-aryl-4,4-dimethoxypiperidines, a solution of 1-N-aryl-piperidin-4-one (1.0 mol. equiv.), trimethyl orthoformate (1.2 mol. equiv.), toluene-p-sulphonic acid, monohydrate, (1.1 mol. equiv.) in methanol (2.7 ml/mmol. of 1-N-aryl-piperidin-4-one) is heated, under reflux, in an atmosphere of nitrogen for 10 minutes. The cooled products are neutralized with 30% methanolic sodium methoxide and filtered. The filtrate is diluted with ether, and the resulting solution is washed twice with water and then with saturated aqueous sodium hydrogen carbonate. The dried (MgSO₄) organic layer is then concentrated under reduced pressure to give the 1-N-aryl-4,4-dimethoxypiperidine.

TABLE 3

| Synthesis of 1-N-aryl-4,4-dimethoxypiperidines | | |
|---|---|---|
| Aromatic substituents | Yield (%) | m.p. (°C.) |
| 2-F | 67 | 69–70 |
| 4-Cl | 68 | 106 |

TABLE 3-continued

| Synthesis of 1-N-aryl-4,4-dimethoxypiperidines | | |
|---|---|---|
| Aromatic substituents | Yield (%) | m.p. (°C.) |
| 3-Cl | 77 | — |
| 2-Cl | 78 | — |

In order to obtain 1-N-aryl-4-methoxy-1,2,5,6-tetrahydropyridines (enol ethers), a solution of 1-N-aryl-4,4-dimethoxypiperidine (1.0 mol. equiv.) and toluene-p-sulphonic acid, monohydrate, (0.01 mol. equiv.) in dichloromethane (2.0 ml/mmol. of 1-N-aryl-4,4-dimethoxypiperidine) is evaporated under reduced pressure. The resulting oil is heated at 150° C. under 20 mmHg pressure for 30–90 minutes. The cooled products are diluted with dichloromethane, neutralized with methanolic sodium methoxide, and then extracted twice with water. The dried (MgSO4) organic layer is evaporated under reduced pressure to give the required enol ether which may then be distilled.

TABLE 4

| Synthesis of 1-N-aryl-4-methoxy-1,2,5,6-tetrahydropyridines (enol ethers) | |
|---|---|
| Aromatic substituents | Yield (%) |
| 2-F | 79 |
| 4-Cl | 62 |
| 3-Cl | 79 |
| 2-Cl | 69 |

Enol ethers were then used to prepare 2'-protected ribonucleoside derivatives.

3',5'-Di-O-acetyluridine (0.312 g) and 1-N-[(2-chloro-4-methyl)phenyl]-4-methoxy-1,2,5,6-tetrahydro-pyridine (1.10 g) were dissolved in dry dioxane (5 ml) at room temperature. A 0.5 M solution of CF3COOH in dioxane (2.6 ml) was then added. The resulting solution was stirred at room temperature for 24 hours and then dry triethylamine (0.35 ml) was added. The products were concentrated under reduced pressure and the residue dissolved in ca 8M methanolic ammonia (10 ml). The resulting solution was stirred at room temperature for 16 hours and the products were then evaporated under reduced pressure. Fractionation of the crude products by chromatography gave the desired 2'-protected uridine derivative (0.39 g) mp 185°-6° C.:

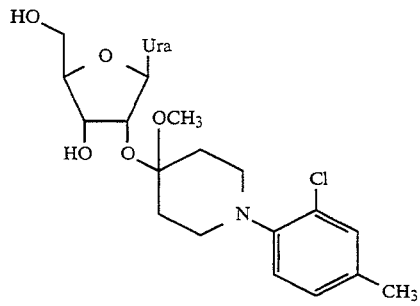

In a further similar example, 3',5'-di-O-acetyluridine (0.328 g) and 1-N-(2-fluorophenyl)-4-methoxy-1,2,5,6-tetrahydropyridine (1.2 g) were dissolved in dry dioxane (5 ml) at room temperature and trifluoroacetic acid (0.1 ml) was added. The reactants were stirred for 24 hours and triethylamine (0.4 ml) was added. The products were concentrated under reduced pressure and redissolved in 8M methanolic ammonia (15 ml). After 36 hours, the solution was evaporated under reduced pressure and the residue was fractionated by chromatography to give the desired uridine derivative in 79% yield:

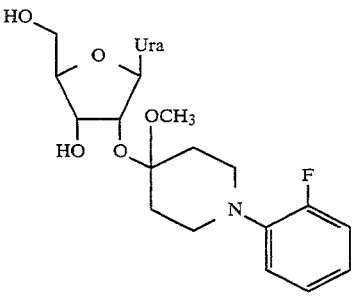

The removal of 2'-protecting groups by acidic hydrolysis at 25° C. was then investigated. Substrates as indicated below (ca 0.5–1.0 mg) were dissolved in 3.0 ml of hydrochloric acid or 0.2M glycine hydrochloride buffer at the specified pH. Aliquots (0.2 ml) of the reaction solutions were removed after suitable intervals of time, neutralized with triethylammonium bicarbonate and analyzed by HPLC (Jones "APEX ODS" column).

The results obtained are presented in the following table:

| Substrate | pH | $t_{\frac{1}{2}}(a)$ | $t_{0.99}(b)$ |
|---|---|---|---|
| | 1.0 | 0.9 min | 6 min |
| | 2.0 | 20.5 min | 136 min |
| | 3.0 | 126 min | 837 min |

(comparison)

-continued
| Substrate | pH | t₁/₂(a) | t₀.₉₉(b) |
|---|---|---|---|
| 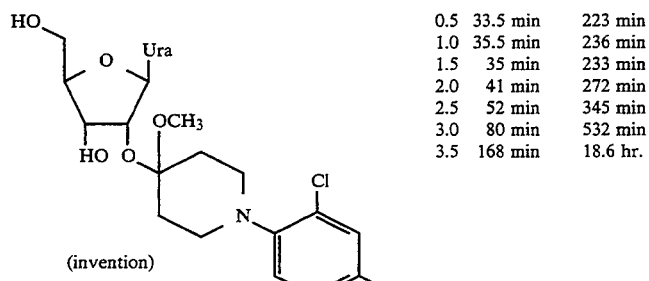<br>(invention) | 0.5<br>1.0<br>1.5<br>2.0<br>2.5<br>3.0<br>3.5 | 33.5 min<br>35.5 min<br>35 min<br>41 min<br>52 min<br>80 min<br>168 min | 223 min<br>236 min<br>233 min<br>272 min<br>345 min<br>532 min<br>18.6 hr. |
| 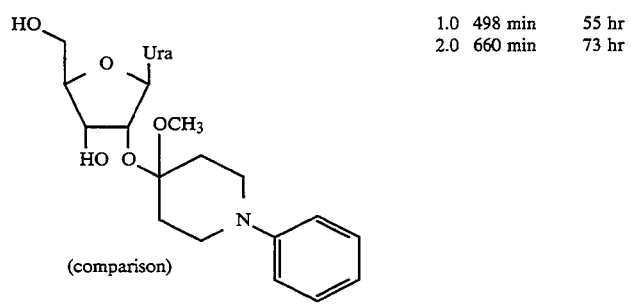<br>(comparison) | 1.0<br>2.0 | 498 min<br>660 min | 55 hr<br>73 hr |
| 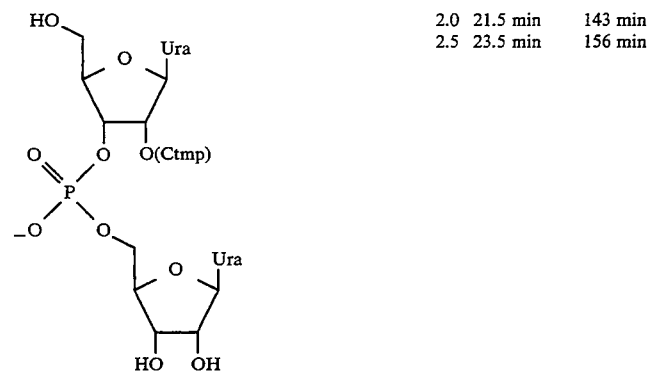 | 2.0<br>2.5 | 21.5 min<br>23.5 min | 143 min<br>156 min |
(This substrate may be obtained by the following scheme:
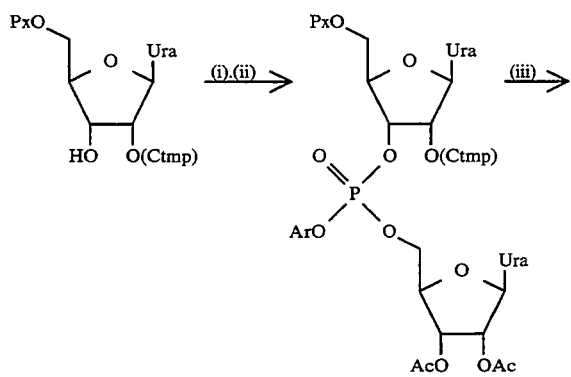

-continued

| Substrate | pH | t½(a) | t₀.₉₉(b) |
|---|---|---|---|

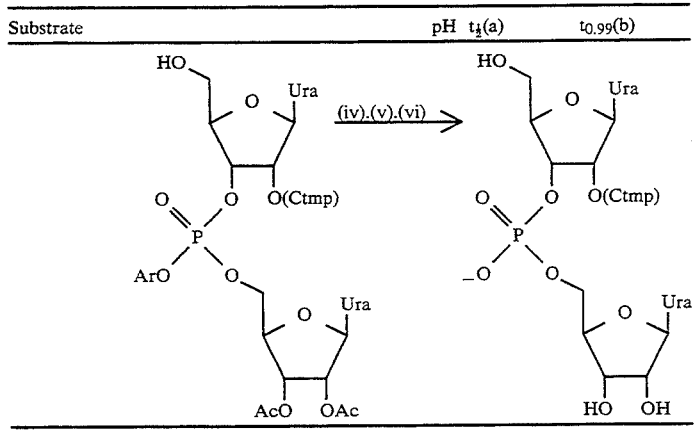

Px=9-phenylxanthen-9-yl; Ar=2-chlorophenyl; Ctmp=1-[(2-chloro-4-methyl)phenyl]-4-methoxypiperidin-4-yl Reagents: (i) (a) 2-chlorophenyl phosphorodi-(1,2,4-triazolide), 1-methylimidazole, tetrahydrofuran, (b) Et₃N, H₂O, tetrahydrofuran; (ii) 2',3'-di-O-acetyluridine, 1-(mesitylene-2-sulphonyl)-3-nitro-1,2,4-triazole, C₅H₅N; (iii) CF₃CO₂H, pyrrole, CH₂Cl₂; (iv) Ac₂O, C₅H₅N;

(v) E-2-nitrobenzaldoxime, N¹,N¹,N³,N³-tetramethylguanidine, dioxane; (vi) aqueous NH₃ (d 0.88).)

(a) t½=half-time; pseudo-first order kinetics were observed for all reactions: straight lines were obtained when logarithms of the percentages of substrates remaining were plotted against time.

(b) t₀.₉₉=calculated time for 99% removal of the 2'-protecting group.

It may be seen from the above Table that, as expected, the rate of hydrolysis of the first-mentioned substrate increases sharply with decreasing pH: thus it is 140 times faster at pH 1.0 than it is at pH 3.0. On the other hand, the rate of hydrolysis of the second-mentioned substrate is virtually unchanged between pH 0.5 and 1.5 and is only ca 2.25 times faster at pH 1.0 than it is at pH 3.0. It is also apparent that the rates of removal of the protecting groups in the first two cases do not differ appreciably in the pH range 2.0–3.0. It may further be seen that the 1-phenyl-4-methoxy-piperidin-4-yl protecting group (the third example) is too stable (i.e. too basic) for the desired purposes. Furthermore, it may be seen that the vicinal phosphotriester group in the partially-protected dinucleoside phosphate (last example) facilitates the acid-catalyzed hydrolysis of the presently-preferred protecting group (Ctmp).

The 2'-O-Ctmp derivative of uridine:

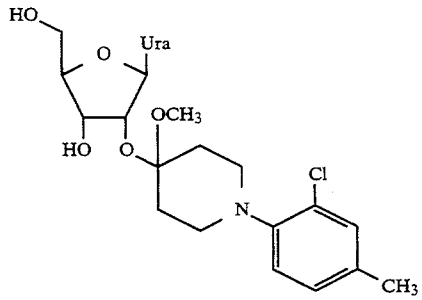

was converted in 91% yield to the following:

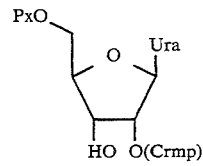

Following the above scheme, the latter compound was then converted by the conventional two-step procedure into the fully-protected dinucleoside phosphate in ca 83% overall yield. When a 0.025M solution of the fully-protected dinucleoside phosphate in dichloromethane was treated with 5.5 mol. equiv. of trifluoroacetic acid and 16.5 mol. equiv. of pyrrole for 30 seconds at room temperature, no starting material remained and the partially-protected dinucleoside phosphate was isolated from the products in 95.5% yield. When the acid treatment of the fully-protected dinucleoside phosphate was extended to 30 minutes under the same conditions, the partially-protected dinucleoside phosphate was isolated in 85% yield. From such results, it may be estimated that less than 0.2% concomitant removal of the 2'-O-Ctmp group occurs in the time required for the complete removal of the 5'-O-(9-phenylxanthen-9-yl) protecting group.

By way of further exemplification of the use of the enol ethers in accordance with the present invention, 1,3-dichloro-1,1,3,3-tetra-isopropyldisiloxane (4.225 g) was added to a stirred suspension of 4-N-(p-t-butylbenzoyl)cytidine (4.5 g) and imidazole (3.645 g) in dry acetonitrile (37 ml) at room temperature. After 1 hour, water (5 ml) was added and the solution was stirred for a further period of 20 minutes. The products were concentrated under reduced pressure, dissolved in chloroform (100 ml), washed with 0.1M hydrochloric acid (2×60 ml) and then with water (2×200 ml). The dried (MgSO₄) organic layer was concentrated under reduced pressure, and the residue was fractionated by chromatography to give a glass (5.8 g). The latter material (2.5 g) was dissolved in dry dichloromethane (10 ml), and 1-N-[(2-chloro-4-methyl)phenyl]-4-methoxy-1,2,5,6-tetrahydropyridine (4.6 g), followed by 0.5M trifluoroacetic acid in dichloromethane (4.6 ml) were added. After 16 hours, the products were neutralized with triethylamine, and then evaporated under reduced pressure. The residue was dissolved in M tetra-ethylammonium fluoride solution in acetonitrile (14.5 ml). After 30 minutes, the products were concentrated under reduced pressure and fractionated by chromatography to give the desired product, which was isolated as a crystalline solid, mp 152° C., in 69% yield.

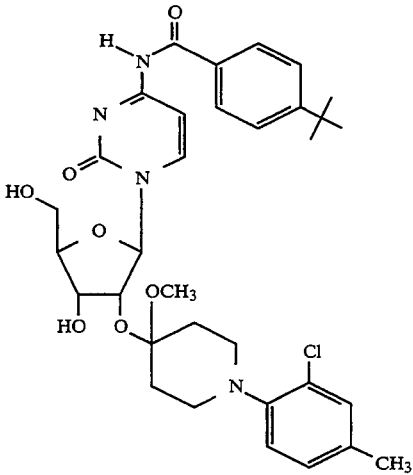

As will be appreciated by those skilled in the art, the present invention is as applicable to 6-N-protected adenosine and 2-N-protected guanosine as it is to uridine and 4-N-protected cytidine derivatives, for example. The application of the present invention will allow the preparation of mononucleotide building blocks (incorporating 1-N-aryl-4-methoxy-piperidin-4-yl protecting groups, such as Ctmp, for example, for the 2'-hydroxy functions of the ribose moieties) that are suitable for the rapid synthesis of oligo- and poly-ribonucleotides (including RNA) both on solid supports and in solution. The substituted 1-N-aryl-piperidin-4-ones described above and the derived acetals and enol ethers, also the respective productions, will be essential integers in the preparation of these building blocks, and hence in their potential commercialization.

Accordingly, the present invention further provides a compound characterized in that it corresponds to the following general formula:

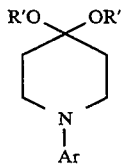

wherein $R^1$ and Ar are as defined above; or a precursor or a derivative thereof.

As an example of a precursor of such an acetal there may be mentioned a corresponding ketone and as an example of a derivative of such an acetal there may be mentioned a corresponding enol ether.

Moreover, the present invention relates to the respective productions.

I claim:

1. A process for protecting the 2'-hydroxyl of a ribonucleoside comprising the reacting of a protected nucleoside of formula I

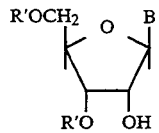

wherein B is a nucleoside heterocyclic base and R' is a hydroxyl-protecting group, with 1-N-aryl-4-alkoxy-1,2,5,6-tetrahydropiperidine of formula II

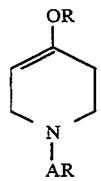

wherein Ar is an aryl group possessing an electron-withdrawing substituent which renders said protecting group acid labile and R is $C_1$–$C_4$ alkyl, in the presence of an acid catalyst and a solvent to yield the compound of formula III below:

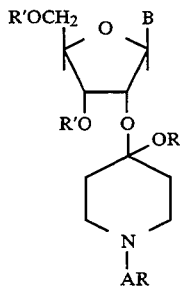

* * * * *